United States Patent [19]

Carstairs et al.

[11] Patent Number: 5,677,019
[45] Date of Patent: Oct. 14, 1997

[54] METHODS OF PRESERVING PLANT MATERIAL

[75] Inventors: Margaret Louise Carstairs, Carnbee Near Anstruthe, Fife, United Kingdom, KY102RU; Lawrence Jennings, Fife, United Kingdom

[73] Assignee: Margaret Louise Carstairs, Fife, United Kingdom

[21] Appl. No.: 704,704

[22] PCT Filed: Mar. 16, 1995

[86] PCT No.: PCT/GB95/00569

§ 371 Date: Oct. 9, 1996

§ 102(e) Date: Oct. 9, 1996

[87] PCT Pub. No.: WO95/24828

PCT Pub. Date: Sep. 21, 1995

[30] Foreign Application Priority Data

Mar. 17, 1994 [GB] United Kingdom ............ 9405233

[51] Int. Cl.$^6$ .................................................. A01N 3/00
[52] U.S. Cl. .................................................. 428/22; 427/4
[58] Field of Search .................... 427/4, 430.1, 412.2, 427/407.1; 428/22

[56] References Cited

U.S. PATENT DOCUMENTS

| | | | |
|---|---|---|---|
| 3,895,140 | 7/1975 | Sheldon et al. ........................... | 428/22 |
| 4,287,222 | 9/1981 | Robinson ................................... | 427/4 |
| 4,664,956 | 5/1987 | Dokkestul et al. ...................... | 428/22 |
| 4,808,447 | 2/1989 | Baker ......................................... | 427/4 |
| 4,828,890 | 5/1989 | Tiedeman et al. ...................... | 428/22 |
| 4,980,194 | 12/1990 | Allison et al. ............................ | 427/4 |
| 5,399,392 | 3/1995 | Sellegaard ................................ | 427/4 |

FOREIGN PATENT DOCUMENTS

| | | |
|---|---|---|
| 0152812 | 8/1985 | European Pat. Off. . |
| 0338469 | 10/1989 | European Pat. Off. . |
| 2028100 | 3/1980 | United Kingdom . |
| 2040669 | 9/1980 | United Kingdom . |

*Primary Examiner*—Diana Dudash
*Attorney, Agent, or Firm*—H. Jay Spiegel

[57] ABSTRACT

The invention provides a method of making preserved plant material having the color and texture of fresh plant material and substantially free from curling or distortion, the method comprising the step of immersing the plant material in an aqueous solution comprising from 40% to 95% by weight of one or more $C_3$–$C_6$ dihydric alcohols at a temperature of from 60° C. to 95° C. The dihydric alcohols preferably comprise a major fraction of propylene glycol. The immersion is preferably carried out for from 5 to 90 minutes at a temperature of from 65° to 85° C. The aqueous solution may also contain dehydrating alcohols and/or polyethylene glycol. The aqueous solution of the dihydric alcohols exchanges for aqueous sap and juices in the plant material, e.g. cut green foliage or cut flowers, without changing the color or texture of the material.

25 Claims, No Drawings

METHODS OF PRESERVING PLANT MATERIAL

The present invention relates to methods of preserving plant material, and in particular to methods of preserving cut green foliage and flowers for use in decorative displays.

At present there is no really satisfactory method of preserving fresh green foliage and freshly cut flowers such as are used in decorative arrangements and displays. The foliage and flowers can be preserved by drying, but this results in drastic shrinkage of flowers, colour changes and brittleness. Other methods attempt to preserve freshly cut flowers and foliage without loss of the fresh plant texture and resilience of the material. For example, it has been known for some time that freshly cut flowers and foliage can be preserved by dipping the cut stems in an aqueous solution of glycerol for a few days. The glycerol is imbibed into the plant material by transpiration and replaces some of the water normally present in the plant material. The glycerol then inhibits saprophytic degradation of the plant material and considerably extends its life. Unfortunately, this method of introducing glycerol into the plant material by making use of the natural transpiration of the plant material (sometimes called perfusion) is extremely slow, even when the conditions of temperature and high relative humidity of the ambient air are optimised. A further difficulty is that glycerol causes drastic colour changes in plant material into which it is absorbed, particularly when that plant material is exposed to light. As a result, it has been found necessary to add dyes to the glycerol solution in order to compensate for the effects of these colour changes. In practice, the use of glycerol as a preservative is restricted to plant materials such as copper beech foliage that do not exhibit a fresh green appearance in their natural state. Yet another problem with preservation of plant material using glycerol solutions is that there frequently occurs bleeding, or weeping, of glycerol solution from the surfaces of the plant material. This is especially apparent in conditions of high relative humidity. Beads of glycerol solution form on the surface of the plant material and may even drip from the plant material. Clearly, this is unsatisfactory and unsightly.

Various attempts have been made to modify or improve the preservation of plant material using glycerol. For example, U.S. Pat. No. 4,287,222 describes a method for preserving cut plant material which comprises immersing the material in pure glycerol at elevated pressure, but at ambient temperature and humidity, in order to effect exchange of glycerol for the aqueous liquid in the plant material. A dye is normally present in the glycerol to compensate for the colour changes caused by the glycerol. However, this technique does not preserve the natural colour of the plant material and does not overcome the problem of bleeding of glycerol in conditions of high relative humidity. In an alternative approach, U.S. Pat. No. 3,895,140 describes the introduction of glycerol into plant material by immersing the plant material in a hot aqueous solution containing 40 to 60% by weight of glycerol and maintained at a temperature of about 70° C. Under these conditions a satisfactory preserved product is obtained after treatment for about 35 to 55 hours. Optionally, the plant material is immersed in the aqueous glycerol at temperatures above 100° C. and at elevated pressure in an autoclave. This reduces the treatment time to 6 to 12 hours. However, the resulting product containing glycerol does not have stable colour and is prone to bleeding. The lengthy treatment times result in very substantial extraction of the natural green colour from the plant material.

Although glycerol remains the preservative of choice for fresh plant material, the substantial drawbacks of glycerol have led some workers in the field to seek alternative preservative compounds. For example, WO91/03160 describes a method of treatment to preserve cut flowers which comprise the steps of, first, drying the flowers over a molecular sieve, followed by immersing the flowers in a solution of polyethylene glycol in a volatile organic solvent such as cellosolve, followed by evaporating residual solvent from the flowers to produce flowers in which substantially all of the water originally present has been replaced by polyethylene glycol. The resulting flowers do not suffer the drawbacks of plant materials containing glycerol. However, the process is extremely expensive and the resulting preserved flowers are costly.

EP-A-0338469 describes a method of preserving plants which allegedly achieves reduced bleeding of the preservative material when the plants are subjected to elevated humidity conditions. The method comprises perfusing the plants by placing the cut stems in an aqueous preservative composition in which the preservative is primarily an alkylene oxide oligomer, 1,3-butanediol, or 1,4-butanediol. The preferred preservatives may be used with lesser amounts of secondary humectant materials selected from glycerol, ethylene glycol, propylene glycol, magnesium chloride or magnesium bromide hexahydrate, and water soluble phosphonate esters. The perfusion step is carried out at a temperature in the range of 20° to 50° C. at a relative humidity in the range of 28 to 80% for a period of one to fourteen days, typically seven to fourteen days. The lengthy perfusion step carried out under controlled conditions renders this process somewhat expensive and slow.

GB-A-2040669 describes a process for the preservation of Douglas Fir needles, wherein the branches, with attached needles, are immersed in a solution comprising (in amounts per liter of solution): 200 to 500 ml water, 200 to 300 ml ethyl alcohol, 0 to 75 ml ethylene glycol, 50 to 75 ml propionic acid, 0 to 20 ml glycerol, 100 to 150 ml formalin, 50 to 175 ml propylene glycol, 40 to 75 g citric acid, 1 to 7 g magnesium sulphate, 15 to 25 g copper sulphate, 5 to 10 g sodium sulphite and 0 to 10 g seaweed extract. The immersion is carried out at ambient temperature for a period of about two weeks. The ethyl alcohol dehydrates the Douglas Fir needles, which then absorb other constituents such as propylene glycol from the solution to provide a preserved Douglas Fir product that shows less tendency to shed its needles than previously known products of this type. Once again, the process is extremely slow, which adds considerable to its expense.

U.S. Pat. No. 4,664,956 describes a method of preserving plant material comprising immersing the material in ethylene glycol having a specific gravity of 1.03–1.10 for a period of 4 hours to 5 days under 21–210 kPa pressure at 21°–41° C.

U.S. Pat. No. 3,895,140, the principal disclosure of which is discussed briefly above, also considers the preservation of cut green foliage by immersing it in hot aqueous solutions of polyhydric alcohols other than glycerol. For example, it mentions the use of hot aqueous solutions containing 40% to 60% of trimethylol propane, pentaerythritol, sorbitol or propylene glycol. The immersion is carried out for 35 to 55 hours at 60° to 70° C. (140° F. to 160° F.). Under these conditions trimethylol propane produced treated green foliage which wilted within 24 hours after drying; pentaerythritol did not appear to be absorbed by the plant tissues, sorbitol wilted the foliage, and propylene glycol produced curled and distorted foliage. In all cases there is substantial extraction of natural colours from the foliage.

It has now been found, surprisingly, that treating plant material by immersion in hot aqueous solutions of low molecular weight dihydric alcohols such as propylene glycol for a relatively short time results in highly effective preservation of the plant material without significantly changing the colour of the plant material. The resulting, preserved plant material has highly stable, natural colour and shows no tendency to bleed on prolonged storage at high relative humidity.

Accordingly, the present invention provides a method of making preserved plant material comprising the step of immersing the plant material in an aqueous solution comprising from 40% to 95% by volume of one or more $C_3$ to $C_6$ dihydric alcohols at a temperature of from 40° C. to 95° C. and for a time sufficient to achieve preservation of the plant material without curling or disturbing the plant material.

Preferably, the aqueous solution comprises from 55% to 80% by volume of the one or more $C_3$ to $C_6$ dihydric alcohols. That is to say, the combined volume of all the $C_3$ to $C_6$ dihydric alcohols in the aqueous solution is in the range of 55% to 80% of the total volume of the liquids making up the aqueous solution. Preferably, the one or more dihydric $C_3$ to $C_6$ alcohols is or are selected from the group consisting of propylene glycol, 1,4-butanediol, 1,3-butanediol, diethylene glycol and triethylene glycol. The most preferred dihydric alcohol is propylene glycol, and preferably the aqueous solution comprises at least 30% by Volume of propylene glycol. More preferably, the aqueous solution comprises at least 40% by volume of propylene glycol. Most preferably, the aqueous solution comprises from 30% to 80% by volume of propylene glycol and from 5% to 50% by volume of 1,4-butanediol. This combination of propylene glycol and 1,4-butanediol appears to give a near-optimal combination of penetrating power, preservative qualities and low volatility desired for the process.

The relatively high temperature at which the process of the invention is carried out, together with the fact that the plant material is immersed (submerged) in the preserving solution and not merely perfused with the preserving solution, means that the dihydric alcohol is exchanged directly for the aqueous liquid present in the plant material at quite high speed and without the need for a preliminary dehydration step or any desiccant to be present in the aqueous solution. However, preferably the aqueous solution does further comprise from 1% to 20% by volume of one or more dehydrating alcohols, such as $C_1$ to $C_5$ monohydric alcohols. That is to say, the combined volume of the $C_1$ to $C_5$ monohydric alcohols in the aqueous solution is preferably 1% to 20% of the total volume of the liquids making up the aqueous solution, more preferably 2% to 10% by volume of the liquids making up the aqueous solution. Preferred monohydric alcohols are methanol, ethanol, propanol and isopropanol.

Preferably, the aqueous solution may also contain from 1% to 20% w/v, preferably from 2% to 10% w/v of polyethylene glycol, preferably in the molecular weight range 200 to 2000.

Preferably, the aqueous solution may contain from 1% to 10% by volume of a trihydric C3–C6 alcohol, such as glycerol, as a secondary humectant. The amount of glycerol used in the aqueous solution is kept low enough to minimise the discoloration and weeping effects of glycerol on the preserved material.

Preferably, the aqueous solution may also contain from 0.01 to 1% by volume of an aldehyde, more preferably a C1–C6 mono- or dialdehyde, such as ethanal or butan-1,5-dial. The aldehyde has been found to modify the mechanical properties of the preserved plant material.

Preferably, the pH of the aqueous solution is kept in the range of from 3 to 9, preferably about 7. The pH is as determined with a conventional glass pH electrode at 25 degrees C.

A particular advantage of the method according to the present invention is that it preserves the natural colour of the plant material, especially the natural green colour of foliage, with minimal leaching of the colour. Another advantage is that the present invention can be applied to freshly cut, partially dried or completely dried foliage or flowers. Unlike previous methods, the method according to the present invention can be used to preserve variegated leaf material without loss of contrast between the differently coloured portions of the variegated leaves. Any colour leaching can be further reduced by adding a colour fixative compound to the aqueous solution. Preferred colour fixative compounds are aluminium or magnesium salts, preferably in an amount of 0.01% to 3% by weight of the aqueous solution.

However, even plant material preserved by the method of the present invention can undergo colour fading on prolonged exposure to sunlight. For this reason, the colour fade of the preserved plant material is preferably reduced by including in the aqueous solution a dissolved transition metal salt, zinc salt or aluminium salt. The said salts are preferably present at a total concentration of 0.01–10% w/v, more preferably 0.1–5% w/v, and most preferably 1.0–4.0% w/v. Preferably, the said salts comprise water-soluble salts of copper or nickel, most preferably copper sulphate. Without wishing to be bound by any theory, it is thought that the transition metal (or zinc or aluminium) ions in the solution substitute for magnesium ions in the plant chlorophyll, and thereby change the photochemical properties of the chlorophyll molecule so that it no longer sensitizes its own decomposition.

A feature of the method according to the present invention is the relatively high temperature of the aqueous solution into which the plant material is immersed. Preferably, the temperature of the aqueous solution is from 65° C. to 85° C. This relatively high temperature results in rapid exchange of the aqueous preservative solution for the natural sap and juices in the plant material. Surprisingly, we do not observe any of the curling or distortion reported in U.S. Pat. No. 3,895,140. It is found that the excessively long treatment times of 35 to 48 hours at 60° to 70° C. taught in U.S. Pat. No. 3,895,140 result in degradation of the plant material and substantial loss of natural colour when the treatment is carried out with the dihydric alcohol solution as in the method of the present invention. In the method of the present invention, the plant material is preferably immersed in the hot aqueous solution for less than 24 hours, more preferably less than 12 hours, still more preferably less than 6 hours, even more preferably less than 3 hours, and most preferably for a total duration of from 5 minutes to 90 minutes.

The optimum immersion time will depend on the temperature of the aqueous treatment solution. Preferably, the treatment temperature multiplied by the treatment time is in the range 200°–18,000° C. minutes, more preferably 300°–9000° C. minutes, most preferably 300°–6000° C. minutes.

The optimum immersion time will also depend on the particular plant material being preserved. For example, extremely fine and delicate plant material such as Maidenhair Fern foliage is typically preserved by immersing in the hot aqueous solution for about 5 minutes. On the other hand, relatively thick and tough foliage such as holly leaves requires immersion for 60 to 90 minutes to achieve complete preservation. The immersion time will also depend on the amount and type of additives, such as dehydrating alcohols, present in the immersion bath. In particular, effective stabilisation of foliage colour by transition metal salts in the aqueous solution may require relatively longer immersion times within the ranges specified above.

The immersion step in the method of the present invention is normally carried out at substantially atmospheric pressure. There is no need to use temperatures above 100° C. and elevated pressures in order to achieve high-speed preservation of the plant material. This is a further advantageous feature of the present invention compared to the existing art.

However, may be advantageous in some cases to carry out the immersion step of the present invention at pressures below atmospheric pressure. In that case, substantially all of the air above the aqueous solution is evacuated for a short time, and air is subsequently readmitted before removing the plant material from the aqueous solution. This reduced-pressure cycling appears to accelerate the preservation process, and allows milder treatment conditions to be used. Thus, the immersion step at reduced pressure is preferably carried out at 40°–50° C., versus 60°–90° C. for immersion carried out entirely at atmospheric pressure. It has been found that the treatment at 40°–50° C. with reduced-pressure cycling is especially useful to preserve leaves such as eucalyptus foliage, which has a surface sheen that is damaged by higher temperature treatments.

Repeated treatment of larger quantities of plant material results in a gradual change in the composition of the aqueous solution. This is because of extraction of water into the solution from the plant material, and also because of evaporation of volatiles from the aqueous solution (there is no requirement for the aqueous solution to be an azeotropic mixture). The composition of the aqueous solution is preferably monitored continuously or intermittently by means of density and/or boiling point or chromatographic measurements, and further dihydric and/or monohydric alcohols are added intermittently to maintain the desired concentrations.

Preferably, the plant material preserved by the method of the present invention is cut green foliage and/or cut flowers. The method is especially suitable for variegated flowers or foliage, and for delicate foliage such as Asparagus Fern or Maidenhair Fern. The method of the present invention is applicable also to the preservation of plant material pigmented with Xanthophyll, Carotene and/or Anthocyanin dyes, with minimal loss of the natural colour due to these dyes.

Preferably, the immersion step is followed by washing the plant material and then drying the surface liquid from the plant material. The washing can be carried out, for example, in warm water at about 40° C. containing a little detergent. The drying step is normally carried out under mild conditions and merely removes surface water from the washed plant material without evaporating any amount of the dihydric alcohol from within the plant material.

In some circumstances it is preferable to combine the hot immersion preservation step of the method according to the present invention with a dip coating step as described below, wherein the preserved plant material is dipped in a polymer solution or suspension following the hot immersion step in order to coat the plant material with a polymer. The preferred polymer comprises polyvinylidene chloride (PVDC).

The present invention also encompasses preserved plant material obtainable by a method according to the invention.

Preferably, the preserved plant material comprises from 5% to 60% by weight of propylene glycol and from 1% to 30% by weight of one or more $C_3$ to $C_6$ dihydric alcohols other than propylene glycol, the weight ratio of the propylene glycol to the combined weight of the second dihydric alcohols being from 1:1 to 20:1. Preferably, the weight ratio is from 2:1 to 20:1, more preferably from 3:1 to 20:1. Preferably, the one or more $C_3$ to $C_6$ dihydric alcohols other than propylene glycol are selected from the group consisting 1,4-butanediol, 1,3-butanediol, diethylene glycol and triethylene glycol.

The preserved plant material according to the present invention has a substantially fresh appearance and exhibits natural colours without any need to add dyes to the preservative solution. The material feels like freshly cut plant material and, in particular, preserved leaves or petals can be bent back through substantially 180° C. without cracking or permanent deformation. The preserved plant material exhibits no tendency to bleed under conditions of high relative atmospheric humidity. Green foliage preserved in this way appears to be entirely stable in air for periods of at least three months.

The preserved plant materials according to the present invention can be distinguished from plant material preserved by imbibing a preservative solution containing propylene glycol, e.g. as described in EP-A-0338469. This is because the lengthy imbibing process results in a high concentration of the preservative solution in the stems of the plant material. In contrast, the process of the present invention tends to result in lower concentrations of preserving solution in the stems than in the leaves of the preserved plant material. Additionally, minor components of the aqueous preserving solutions used in the process of the present invention, for example copper salts, are readily detectable in the preserved plant material.

The method of the present invention preferably further comprises the step of dipping the plant material in an aqueous solution or suspension of one or more polymers, followed by drying to provide a layer of polymer on the surface of the plant material.

The dipping step coats the plant material with a thin layer of the polymer. The thin layer of the polymer helps to maintain the structure and flexibility of the plant material and, most importantly, substantially prevents shrinkage of the plant material on drying. The thin layer of polymer also inhibits saprophytic degradation of the plant material. This method is found to be particularly suitable for preserving cut flowers.

The aqueous solution or suspension can be an emulsion or latex of one or more polymers that are not themselves soluble in water. Preferably, the one or more polymers comprises a cellulose derivative, a starch derivative, a natural gum, an alginate, polyvinyl pyrrolidone, polyvinyl acetate or polyvinyl alcohol. More preferably, the aqueous solution or suspension comprises 5–15% w/v of carboxymethyl cellulose, 4–10% w/v of polyvinyl acetate, and a surfactant. Good results are also obtained by replacing the polyvinyl acetate with polyvinyl alcohol.

Preferably, the aqueous solution or suspension comprises from 10% to 50% v/v of one or more water-miscible organic solvents, preferably methanol. The presence of the organic solvents results in accelerated drying of the polymer film, and appears to reduce any tendency of the polymer film to delaminate from the plant material.

The dip coating step is used as an adjunct to the preservation method based on immersion in a hot solution of dihydric alcohol described above.

Advantages of the method and preserved plant material according to the present invention include low cost, high speed and excellent quality of the product.

Specific embodiments of the method and preserved plant materials according to the present invention will now be described further in and by the following Examples.

EXAMPLE 1

The preservative effect of the method according to the present invention is demonstrated as follows.

A preserving solution is made up from 500 ml of propylene glycol, 500 ml of 1,4-butanediol and 100 ml water. The solution is heated to 80° C. and freshly cut carnations are immersed in the solution for 20 minutes. Following this treatment, the carnations are washed briefly in warm water and drained. The treated carnations have the colour, turgor and resilience of fresh natural carnation blooms. The superior preservation of the treated carnations is demonstrated by comparing the weight of the treated carnations (sample A) and untreated, fresh carnations (Sample B) when each is hung in a dry box over silica gel at ambient temperature for a period of one week:

| Day | Wt. of Sample A | Wt. of Sample B |
|-----|-----------------|-----------------|
| 1 | 10.73 g | 8.62 g |
| 2 | 10.17 g | 6.87 g |
| 3 | 9.98 g | 5.62 g |
| 4 | 9.26 g | 4.45 g |
| 5 | 9.19 g | 4.00 g |
| 6 | 9.07 g | 3.97 g |
| 7 | 9.95 g | 3.70 g |

At the end of 7 days, the treated carnations still had natural colour and turgor, whereas the untreated carnations had become dry, shrunken and brittle.

EXAMPLE 2

The effect of varying the treatment temperature in the method of the present invention is demonstrated as follows.

An aqueous preserving solution as described in Example 1 is prepared. Samples of ivy leaves are placed in aliquots of this solution at ambient temperature, and the samples are then ramped quickly to preselected final treatment temperatures and held at the preselected temperatures for 20 minutes. The ivy leaves are then removed, washed briefly in warm water, air dried and examined for appearance, texture and quality of preservation. The results are as follows:

| Final Treatment Temperature | Quality |
|------|------|
| 40° C. | poor—limp |
| 50° C. | poor—limp |
| 60° C. | fair—slightly wrinkled |
| 70° C. | good |
| 80° C. | good |
| 90° C. | fair—slightly discoloured |
| 100° C.* | poor—loss of colour |
| 110° C.* | poor—loss of colour |

*Comparative Examples

The ivy leaves preserved at 60°–90° C. showed excellent stability on prolonged storage in air for 2–3 months. In particular, the leaves did not dry out, shrink or become brittle. The leaves did not undergo the discoloration normally observed with glycerol treatment, nor was there any bleeding of the preservative solution from the leaves.

EXAMPLE 3

The high speed of the preserving method according to the present invention is demonstrated by the following experiment.

A preserving solution is made up from 600 ml propylene glycol, 100 ml 1,4-butanediol, 100 ml isopropanol and 220 ml water. A sprig of gloxia leaves is weighed and then immersed in the preserving solution at 80° C. At intervals the sprig is removed, washed in warm water, dried of surface liquid, and weighed. The results are as follows:

| Time (minutes) | Weight (g) |
|----------------|------------|
| 0 | 1.592 |
| 1 | 1.422 |
| 10 | 1.614 |
| 20 | 1.672 |
| 30 | 1.695 |
| 40 | 1.704 |
| 50 | 1.704 |
| 60 | 1.704 |

It can be seen that there is an initial weight loss, probably due to extraction of water from the leaves, followed by a weight gain as the preservative solution is absorbed. A steady state corresponding to complete absorption of the preservative solution is reached after about 40 minutes. The gloxia leaves treated for 40 minutes exhibit a fresh, natural appearance and texture and excellent stability in air for 2–3 months or more. No further improvement in preservation is seen in the samples treated for 60 minutes.

Similar results are obtained for other leaf materials, for example, a laurel leaf was found to reach a steady weight after 50 minutes at 80° C. in the above preserving solution. A rose leaf reached a steady weight after 30 minutes under the same conditions. Clearly, the minimum treatment time needed varies with the thickness and toughness of the foliage being treated, but in any case is likely to be less than 90 minutes at 80° C.

EXAMPLE 4

The effect of varying the composition of the preserving solution is illustrated as follows.

A number of preserving solutions are made up and used to treat ivy leaves at 80° C. for 40 minutes. The treated ivy leaves are evaluated for colour, turgor, flexibility and storage properties.

| Sample | A* | B | C | D |
|--------|-----|-----|-----|-----|
| Propylene Glycol | 30% | 50% | 70% | 90% |
| Water | 70% | 50% | 30% | 10% |
| Result | poor | fair | good | poor |

| Sample | E | F | G | H* |
|--------|-----|-----|-----|-----|
| Propylene Glycol | 30% | 50% | 60% | 90% |
| 1,4-butanediol | 10% | 10% | 10% | 10% |
| Water | 60% | 40% | 30% | — |
| Result | fair | good | good | poor |

| Sample | I* | J | K | L |
|--------|-----|-----|-----|-----|
| Propylene Glycol | 30% | 50% | 60% | 80% |
| 1,4-butanediol | 5% | 5% | 5% | 5% |
| Isopropanol | 5% | 5% | 5% | 5% |
| Water | 60% | 40% | 30% | 20% |

-continued

| Result | poor | good | excellent | good |
|---|---|---|---|---|
| Sample | | | M | |
| Propylene Glycol | | | 150 ml | |
| PEG 2000 | | | 20 g | |
| Isopropanol | | | 10 ml | |
| Water | | | 10 ml | |
| Result | | | good | |

PEG 2000 is a polyethylene glycol mixture having an average molecular weight of 2000. The percentages given above are by volume. Asterisks (*) denote comparative examples.

Comparative experiments were also carried out by immersing ivy leaves in 60% and 80% v/v glycerol/water solutions and in 50% and 75% v/v ethylene glycol (ethanediol) aqueous solutions at 80° C. for up to one hour. In all cases the leaves rapidly discoloured, turning brown. In addition, the glycerol solution caused the leaves to wrinkle. The leaves only recovered their turgor after treatment for 16 hours or more in the hot glycerol solution. This may explain the lengthy treatment times taught in U.S. Pat. No. 3,895,140.

The above embodiments have been described by way of example only. Many other embodiments falling within the scope of the accompanying claims will be apparent to the skilled reader.

We claim:

1. A method of making preserved plant material comprising the step of immersing the plant material in an aqueous solution comprising from 40% to 95% by volume of one or more $C_3$-$C_6$ dihydric alcohols at a temperature of from 40° C. to 95° C. and for a time sufficient to achieve preservation of the plant material without curling or distorting the plant material.

2. A method according to claim 1, wherein the aqueous solution comprises from 55% to 80% by volume of the one or more $C_3$-$C_6$ dihydric alcohols.

3. A method according to claim 1 or 2, wherein the one or more dihydric $C_3$-$C_6$ alcohols are selected from the group consisting of propylene glycol, 1,4-butanediol, 1,3-butanediol, diethylene glycol and triethylene glycol.

4. A method according to claim 1 or 2, wherein the aqueous solution comprises at least 30% by volume of propylene glycol.

5. A method according to claim 1 or 2, wherein the aqueous solution comprises at least 40% by volume of propylene glycol.

6. A method according to claim 1 or 2, wherein the aqueous solution comprises from 30% to 80% by volume of propylene glycol and from 5% to 50% by volume of 1,4-butanediol.

7. A method according to claim 1 or 2, wherein the aqueous solution further comprises from 1% to 20% by volume of one or more $C_1$-$C_5$ monohydric alcohols.

8. A method according to claim 7, wherein the aqueous solution comprises from 2% to 10% by volume of the $C_1$-$C_5$ monohydric alcohols.

9. A method according to claim 8, wherein the $C_1$-$C_5$ monohydric alcohols are selected from the group consisting of methanol, ethanol, propanol and isopropanol.

10. A method according to claim 1 or 2, wherein the aqueous solution further comprises one or more dissolved salts of a transition metal, aluminum or zinc.

11. A method according to claim 10, wherein said dissolved salts are present in an amount of 0.01–10% w/v, preferably 0.1–5% w/v, and more preferably 1.0–4.0% w/v.

12. A method according to claim 11, wherein the dissolved salts comprise copper or nickel salts.

13. A method according to claim 1 or 2, wherein the plant material is immersed in the aqueous solution at a temperature of from 65° C. to 85° C.

14. A method according to claim 1 or 2, wherein the plant material is immersed in the aqueous solution for less than 24 hours.

15. A method according to claim 1 or 2, wherein the plant material is immersed in the aqueous solution for less than 12 hours.

16. A method according to claim 1 or 2, wherein the plant material is immersed in the aqueous solution for less than 6 hours.

17. A method according to claim 1 or 2, wherein the plant material is immersed in the aqueous solution for less than 3 hours.

18. A method according to claim 1 or 2, wherein the plant material is immersed in the aqueous solution for a total duration of from 5 minutes to 90 minutes.

19. A method according to claim 1 or 2, wherein the plant material is cut green foliage and/or cut flowers.

20. A method according to claim 1 or 2, wherein the immersion step is followed by washing the plant material and drying surface liquid from the plant material.

21. A method according to claim 1 or 2, wherein at least part of the immersion step is carried out at a pressure below atmospheric pressure.

22. Preserved plant material obtainable by a method according to claim 1 or 2.

23. Preserved plant material according to claim 22, comprising from 5% to 60% by weight of propylene glycol and from 1% to 30% by weight of one or more $C_3$-$C_6$ dihydric alcohols other than propylene glycol, the weight ratio of the propylene glycol to the second dihydric alcohols being 1:1 to 20:1.

24. Preserved plant material according to claim 23, wherein the one or more $C_3$-$C_6$ dihydric alcohols are selected from the group consisting of 1,4-butanediol, 1,3-butanediol, diethyleneglycol and triethylene glycol.

25. A method of preserving plant material according to any of claims 1 or 2, further comprising the step of dipping the plant material in an aqueous solution or suspension of one or more polymers, followed by drying to leave a layer of polymer on the surface of the plant material.

* * * * *